(12) United States Patent
Berdugo Polak

(10) Patent No.: US 11,911,505 B2
(45) Date of Patent: Feb. 27, 2024

(54) LIQUID FORMULATIONS OF HYPOGLYCAEMIC SULFONAMIDES

(71) Applicant: AMMTEK, Paris (FR)

(72) Inventor: Marianne Berdugo Polak, Paris (FR)

(73) Assignee: AMMTEK, Paris (FR)

( * ) Notice: Subject to any disclaimer, the term of this patent is extended or adjusted under 35 U.S.C. 154(b) by 119 days.

(21) Appl. No.: 17/412,305

(22) Filed: Aug. 26, 2021

(65) Prior Publication Data

US 2021/0378956 A1   Dec. 9, 2021

Related U.S. Application Data

(62) Division of application No. 14/380,080, filed as application No. PCT/FR2013/050421 on Feb. 28, 2013, now Pat. No. 11,110,059.

(30) Foreign Application Priority Data

Feb. 28, 2012  (FR) ..................... 1251795

(51) Int. Cl.
| | | |
|---|---|---|
| *A61K 9/10* | (2006.01) | |
| *A61K 47/38* | (2006.01) | |
| *A61K 31/64* | (2006.01) | |
| *A61K 9/00* | (2006.01) | |

(52) U.S. Cl.
CPC ............ *A61K 9/10* (2013.01); *A61K 9/0048* (2013.01); *A61K 31/64* (2013.01); *A61K 47/38* (2013.01)

(58) Field of Classification Search
CPC ...... A61K 31/64; A61K 47/38; A61K 9/0048; A61K 9/10; A61P 25/00; A61P 27/00; A61P 27/02; A61P 27/16; A61P 3/00; A61P 3/10
See application file for complete search history.

(56) References Cited

U.S. PATENT DOCUMENTS

| | | |
|---|---|---|
| 4,313,765 A | 2/1982 | Baird et al. |
| 11,110,059 B2 | 9/2021 | Berdugo Polak |
| 2003/0096000 A1 | 5/2003 | Solis et al. |
| 2005/0019412 A1 | 1/2005 | Bosch et al. |
| 2006/0166871 A1 | 7/2006 | Minamitake et al. |
| 2008/0279928 A1 | 11/2008 | Moschwitzer |
| 2010/0233255 A1 | 9/2010 | Moinet et al. |
| 2011/0212169 A1 | 9/2011 | Bae et al. |
| 2012/0225947 A1 | 9/2012 | Polak et al. |

FOREIGN PATENT DOCUMENTS

| | | |
|---|---|---|
| JP | 2002-525311 | 8/2002 |
| JP | 2004-532252 | 10/2004 |
| JP | 2008-536812 | 9/2008 |
| JP | 2009-051761 | 3/2009 |
| JP | 2009-102389 | 5/2009 |
| JP | 2009-523139 | 6/2009 |
| JP | 2009-543777 | 12/2009 |
| WO | WO 2000/18374 | 4/2000 |
| WO | WO 02/11716 | 2/2002 |
| WO | WO 2003/034991 | 5/2003 |
| WO | WO 2008/008364 | 1/2008 |
| WO | WO 2008/015226 | 2/2008 |
| WO | WO 2011/036202 | 3/2011 |
| WO | WO 2011/107855 | 9/2011 |
| WO | WO 2012/076691 | 6/2012 |

OTHER PUBLICATIONS

Pithadia, A. B. et al. "Reversal of experimentally induced seizure activity in mice by glibenclamide" *Annals of Neurosciences*, Jan. 2013, pp. 10-12, vol. 20, No. 1.
Subils, T. et al., "Effect of preservatives on Shiga toxigenic phages and Shiga toxin of *Escherichia coli* O157:H7" *J Food Prot.*, May 2012, pp. 1-2 (abstract only), vol. 75, No. 5.
Hassan, Z. et al., "Hypoglycaemic Effects of Aqueous Extract of Gynura Procumbens" *Pharmacology online*, 2008, pp. 30-50, No. 1.
Di Folco, U. et al. "Stability of Three Different Galenic Liquid Formulations Compounded from Tablet Containing Glibenclamide" *Journal of Nutritional Therapeutics*, 2012, pp. 152-160, vol. 1, No. 2.
Cirri, M. et al., "Fast-Dissolving Tablets of Glyburide Based on Ternary Solid Dispersions with PEG 6000 and Surfactants" *Drug Delivery*, 2007, pp. 247-255, vol. 14.
Royal Pharmaceutical Society, "Pharmaceutical Issues when Crushing, Opening or Splitting Oral Dosage Forms" Jun. 2011, pp. 1-7.

*Primary Examiner* — Jean P Cornet
(74) *Attorney, Agent, or Firm* — SALIWANCHIK, LLOYD & EISENSCHENK

(57) ABSTRACT

The present invention relates to a liquid pharmaceutical formulation of hypoglycaemic sulfonamide, intended for oral or ophthalmic administration. The present invention relates in particular to an oral formulation particularly suitable for paediatric use.

6 Claims, 1 Drawing Sheet

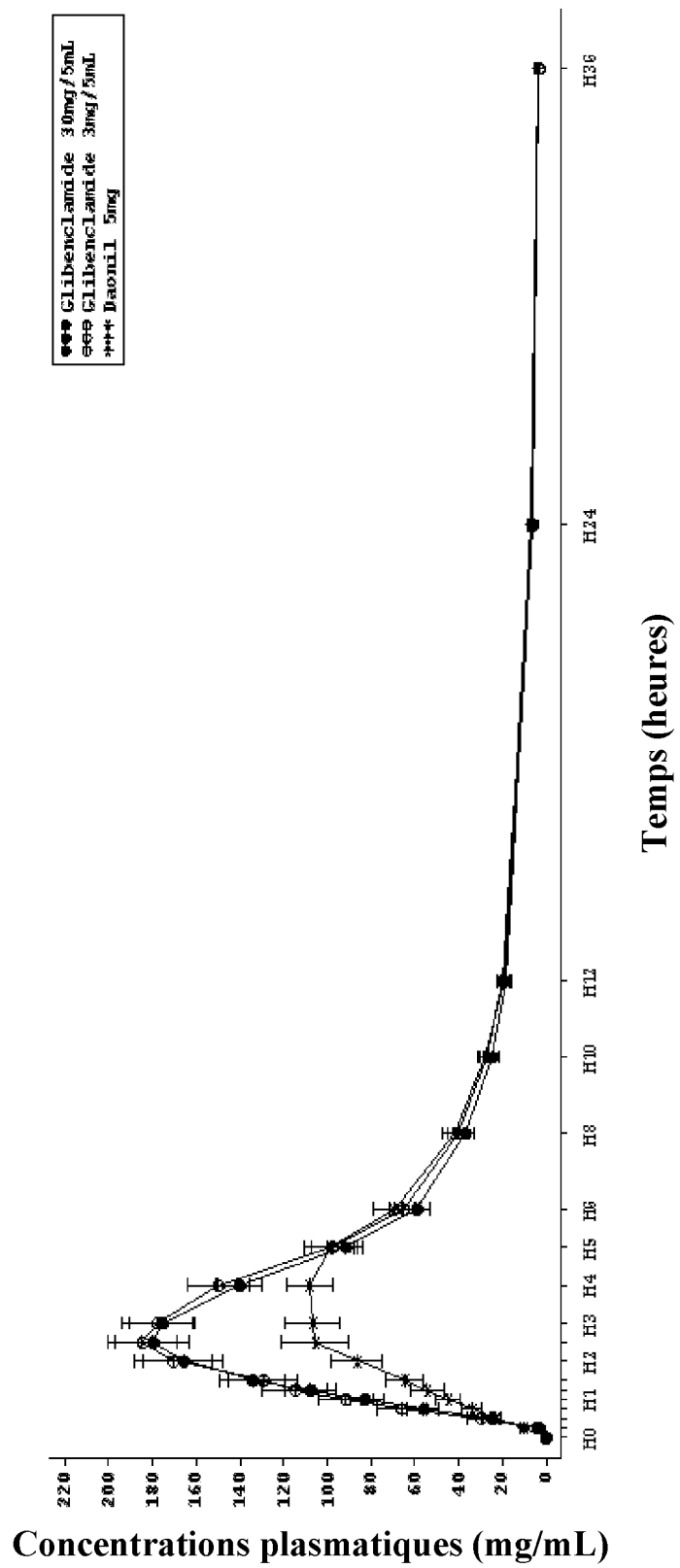

LIQUID FORMULATIONS OF HYPOGLYCAEMIC SULFONAMIDES

CROSS-REFERENCE TO RELATED APPLICATIONS

This application is a divisional of U.S. application Ser. No. 14/380,080, filed Aug. 21, 2014, now U.S. Pat. No. 11,110,059, which is the U.S. national stage application of International Patent Application No. PCT/FR2013/050421, filed Feb. 28, 2013.

The present invention relates to the field of pharmaceutical formulations, and more specifically to that of formulations suitable for paediatric, geriatric or veterinary use.

TECHNOLOGICAL BACKGROUND OF THE INVENTION

Glibenclamide or 5-chloro-N-[2-[4-(cyclohexylcarbamoylsulfamoyl)phenyl]ethyl]-2-methoxybenzamide (UIPAC nomenclature) is an inhibitor of ATP-dependent potassium channels ($K_{ATP}$) present on the surface of pancreatic cells. Like glucose, it acts by stimulating the secretion of insulin by pancreatic β cells. This compound, also known by the name glyburide (USAN), belongs to the sulfonylurea family and is commonly used in the treatment of type 2 diabetes.

Like all hypoglycaemic sulfonamides, glibenclamide can cause hypoglycaemia leading to convulsions, coma and even death. Accurate dosing of this compound in relation to the patient's weight and/or glycaemic equilibrium is therefore essential in order to prevent such side effects.

Currently, glibenclamide is only available in tablet form. This pharmaceutical form is totally unsuitable for oral administration in young children or infants, or in the elderly who may have difficulty taking tablets. For these patients, one or more glibenclamide tablets can be reduced to powder and the required dose of powder is dissolved in a liquid, for example in water. However, these practices result in important variations in the amount of active substance administered and can also induce variations in the rate of release of the active substance depending on the extent to which the tablet is crushed. These variations are mainly due to uncertainties about the suspension and the particle size of the crushed tablet as well as to the very low solubility of glibenclamide (solubility in water at 27° C.: 4 mg/L) which heightens the risk of settling.

Now, infants, particularly premature infants, young children and elderly persons are the populations the most exposed to hypoglycaemic accidents. It is therefore essential that the dose administered to these patients be as accurate as possible.

Furthermore, hypoglycaemic sulfonamides, notably glibenclamide, have recently been found to be especially useful in the treatment of ocular disorders (WO 2011/036202 and WO 2008/015226). Yet to date, there is no formulation of these compounds suitable for administration by the ophthalmic route, in particular by topical application.

Consequently, there is a real need for a liquid formulation of hypoglycaemic sulfonamide, and more particularly of glibenclamide, which is suitable for administration by the ophthalmic route or for administration by the oral route in patients for whom the use of tablets is not indicated, said formulation preferably having acceptable organoleptic properties.

SUMMARY OF THE INVENTION

The inventors have developed a pharmaceutical formulation of hypoglycaemic sulfonamide whose properties are compatible with administration by the oral route, in particular to infants, particularly premature infants, young children or persons who may have difficulty taking tablets, or with administration by the ophthalmic route.

Thus, the present invention relates to a liquid pharmaceutical formulation comprising micronised particles of hypoglycaemic sulfonamide, preferably 90% of the particles having a size less than 30 μm, at least one thickener, and a buffer system allowing the pH of said formulation to be maintained between 4 and 8.

The formulation can comprise at least one thickener selected from the group consisting of polysaccharides, cellulose derivatives and gelling carbomers, and combinations thereof, preferably from the group consisting of polysaccharides and cellulose derivatives.

In particular the formulation can comprise at least one thickener which is a cellulose derivative, preferably selected from the group consisting of hydroxyalkylcellulose, methylcellulose, ethylcellulose, ethylmethylcellulose, carboxymethylcellulose, sodium carboxymethylcellulose, and a combination thereof. In particular, the hydroxyalkylcellulose can be selected from the group consisting of hydroxyethylcellulose, hydroxymethylcellulose, hydroxypropylcellulose, and hydroxypropylmethylcellulose, and a combination thereof. In an especially preferred manner, the formulation comprises hydroxyethylcellulose as a thickener.

The formulation can comprise at least one thickener which is a polysaccharide, preferably selected from the group consisting of xanthan gum, tragacanth, carrageenan, galactomannan, gellan gum, gum arabic, karaya gum, pectin, starch and its derivatives obtained by esterification or etherification, and tamarind, and a combination thereof. In an especially preferred manner, the formulation comprises xanthan gum as a thickener.

The formulation can comprise at least one thickener which is a gelling carbomer, preferably selected from the group consisting of CARBOPOL 934P, CARBOPOL 71G, CARBOBOL 971P and CARBOBOL 974P, and a combination thereof.

Preferably, the formulation comprises hydroxyethylcellulose and xanthan gum as thickeners.

The formulation according to the invention can comprise at least one preservative, preferably selected from the group consisting of benzoic acid and its sodium or potassium salts, parabens, sorbic acid and its sodium or potassium salts, quaternary ammoniums, mercury derivatives, and a combination thereof. In an especially preferred manner, the preservative is sodium benzoate.

The formulation according to the invention can comprise a buffer system maintaining the formulation at a pH comprised between 4 and 6, preferably selected from the group consisting of lactic acid/sodium citrate, citric acid/ $Na_2HPO_4$, citric acid/sodium citrate and acetic acid/sodium acetate systems. In an especially preferred manner, the buffer system is composed of sodium citrate and lactic acid.

Alternatively, the formulation can comprise a buffer system maintaining the formulation at a pH comprised between 6 and 8, preferably selected from the group consisting of acetic acid/sodium acetate, boric acid, boric acid/sodium acetate, boric acid/sodium propionate and $Na_2HPO_4$/$NaH_2PO_4$ systems.

In an especially preferred manner, the formulation comprises a buffer system maintaining the formulation at a pH comprised between 4.5 and 5.5, preferably a buffer system composed of sodium citrate and lactic acid.

The hypoglycaemic sulfonamide can be selected from the group consisting of glibenclamide, chlorpropamide, glibornuride, gliclazide, glimepiride, glipizide, glybutamide, glybuzole, glycyclamide, glymidine sodium, metahexamide, phenbutamide, gliquidone, tolbutamide, tolazamide, acetohexamide, carbutamide, glyclopyramide and glisoxepide, and a combination thereof. Preferably the hypoglycaemic sulfonamide is selected from the group consisting of glibenclamide, glimepiride, gliquidone and acetohexamide, and a combination thereof. In an especially preferred manner, the hypoglycaemic sulfonamide is glibenclamide.

The formulation can comprise between 0.01 and 100 mg/mL of hypoglycaemic sulfonamide, preferably between 0.1 and 10 mg/mL.

According to a preferred embodiment, at least 90% of the micronised particles have a size less than 30 µm, preferably less than 10 µm.

The formulation according to the invention can comprise a mixture of thickeners composed of approximately 50% hydroxyethylcellulose and approximately 50% xanthan gum.

Preferably, the formulation has a viscosity comprised between 350 and 450 mPa·s.

The formulation can have an osmolality less than 400 mOsm/L, preferably less than 250 mOsm/L.

According to a preferred embodiment, the formulation comprised between 0.1 and 10 mg/mL of hypoglycaemic sulfonamide, between 8 and 15 mg/mL of thickener(s), and between 0.5 and 10 mg/mL of preservative(s).

In particular, the formulation can comprise between 0.1 and 10 mg/mL of glibenclamide, approximately 5 mg/mL of hydroxyethylcellulose, approximately 5 mg/mL of xanthan gum, approximately 5 mg/mL of sodium benzoate, and a buffer system composed of sodium citrate and lactic acid maintaining the pH at about 4.8.

It can be packaged in a container comprising, or being associated with, a volumetric delivery system. It can also be packaged in a single dose container.

The formulation can be intended for administration by the oral, rectal, vaginal or ophthalmic route, in particular by topical application in the eye. Preferably, the formulation is intended for administration by the oral route or by the ophthalmic route. In an especially preferred manner, the formulation is intended for administration by the oral route.

The formulation according to the invention can be used in the treatment of diseases in humans or animals. In particular, the formulation can be used in infants, particularly premature infants, young children and persons, particularly elderly persons, for whom taking tablets is difficult, for example persons with swallowing disorders.

The disease to be treated can be selected from the group consisting of type 2 diabetes, monogenic diabetes mellitus such as neonatal diabetes, juvenile diabetes involving the same molecular mechanisms as neonatal diabetes, mitochondrial diabetes associated with deafness (MIDD, Maternally Inherited Diabetes and Deafness) or MODY diabetes (Maturity Onset Diabetes of the Young), transient neonatal hyperglycaemia, a neuropsychological, muscular or neurological disorder and diseases associated with retinal ischaemia and/or retinal excitotoxicity. Preferably, the disease to be treated is type 2 diabetes, transient neonatal hyperglycaemia or neonatal diabetes. In an especially preferred manner, the disease to be treated is type 2 diabetes or neonatal diabetes.

BRIEF DESCRIPTION OF THE DRAWINGS

FIG. 1 shows the mean plasma concentration profiles obtained with two formulations of glibenclamide according to the invention (0.6 mg/mL and 6 mg/mL) and that of a DAONIL tablet crushed in water.

DETAILED DESCRIPTION OF THE INVENTION

The inventors have developed a liquid hypoglycaemic sulfonamide formulation suitable for administration by the oral route or by the ophthalmic route. In particular the inventors have developed a formulation that is especially suitable for oral administration in paediatric use. Pharmaceutical formulations suitable for paediatric needs fulfill specific criteria that are not necessarily taken into consideration for formulations intended for adults. For instance, paediatric formulations are preferably liquid formulations, with an acceptable taste, little or no odor, and allowing the administration of accurate doses that vary according to age, weight and the requirements of young patients. The development of liquid formulations for oral administration of hypoglycaemic sulfonamides is all the more complex in that they are often used in the treatment of disorders of glycaemia, and that their formulation preferably does not, therefore, comprise any sugar-based sweetener or sweetening agent.

Thus, according to a first aspect, the present invention relates to a liquid pharmaceutical formulation comprising micronised particles of a sulfonamide, in particular a hypoglycaemic sulfonamide, 90%, or at least 90%, of the particles having a size less than 30 µm, at least one thickener, and a buffer system.

The sulfonamides are substituted derivatives of sulfonamide. In particular, these compounds can have an antimicrobial, diuretic or hypoglycaemic activity. Hypoglycaemic sulfonamides are a class of compounds comprising a sulfonyl group bonded to a urea group. They act mainly by stimulating insulin secretion by binding to the SUR subunit of Kir6.2/SUR1 channels. These channels are also present in the brain (Liss et al., 2001) where they contribute to the protection of the central nervous system (CNS) against ischaemia. The inhibitors of these channels also have a retinal neuroprotective effect and can therefore be used in the treatment of retinal diseases, particularly diseases associated with ischaemia or with retinal excitotoxicity phenomena (WO 2011/036202).

According to one embodiment, the hypoglycaemic sulfonamide is selected from the group consisting of glibenclamide, chlorpropamide, glibornuride, gliclazide, glimepiride, glipizide, glybutamide, glybuzole, glycyclamide, glymidine sodium, metahexamide, phenbutamide, gliquidone, tolbutamide, tolazamide, acetohexamide, carbutamide, glyclopyramide and glisoxepide, and a combination thereof. According to another embodiment, the hypoglycaemic sulfonamide is selected from the group consisting of glibenclamide, chlorpropamide, glibornuride, gliclazide, glimepiride, glybutamide, glybuzole, glycyclamide, glymidine sodium, metahexamide, phenbutamide, gliquidone, tolbutamide, tolazamide, acetohexamide, carbutamide, glyclopyramide and glisoxepide, and a combination thereof.

According to a particular embodiment, the hypoglycaemic sulfonamide has a solubility in water at 27° C. of less than 100 mg/L, preferably less than 50 mg/L and even more preferably less than 25 mg/L. In particular, the hypoglycaemic sulfonamide can be selected from the group consisting of glibenclamide (solubility in water at 27° C.: 4 mg/L), glimepiride (solubility in water at 27° C.: 38 mg/L), glipizide (solubility in water at 27° C.: 16 mg/L), gliquidone (solubility in water at 27° C.: 2 mg/L) and acetohexamide (solubility in water at 27° C.: 48 mg/L), and a combination thereof. Preferably, the hypoglycaemic sulfonamide is selected from the group consisting of glibenclamide, glimepiride, gliquidone and acetohexamide, and a combination thereof.

According to a preferred embodiment, the hypoglycaemic sulfonamide is glibenclamide.

The formulation according to the invention is a suspension comprising micronised particles of a hypoglycaemic sulfonamide. In order to obtain satisfactory pharmacokinetics, 90% of the particles have a size less than 30 µm. According to a particular embodiment, 75% of the particles have a size less than 10 µm. According to a preferred embodiment, 90% of the particles have a size less than 10 µm.

The techniques for obtaining micronised particles are well known to a person skilled in the art (see for example patent EP 0362704). The micronisation can be obtained in particular by provoking high-speed collisions between the particles which causes them to break up into smaller particles. The techniques for measuring the size, or diameter, of micronised particles are also well known to a person skilled in the art.

According to a particular embodiment, at least 90% of the micronised particles have a size less than 30 µm, preferably at least 95% or 99%. In an especially preferred manner, 100% of the micronised particles have a size less than 30 µm.

According to another particular embodiment, at least 75%, preferably at least 90, 95 or 99% of the particles have a size less than 10 µm. In an especially preferred manner, 100% of the micronised particles have a size less than 10 µm.

According to a preferred embodiment, at least 90%, preferably at least 95 or 99%, of the micronised particles have a size less than 30 µm and at least 75%, preferably at least 90, 95 or 99% of the micronised particles have a size less than 10 µm.

Preferably, at least 50% of the particles have a size less than 5 µm. In an especially preferred manner, 25%, or at least 25%, of the particles have a size less than 1 µm.

The concentration of hypoglycaemic sulfonamide is easily adjusted by a person skilled in the art according to the nature of the compound and the targeted patient population.

According to one embodiment, the formulation comprises between 0.1 and 100 mg/mL of hypoglycaemic sulfonamide, preferably between 0.05 and 20 mg/mL, even more preferably between 0.1 and 10 mg/mL. According to a particular embodiment, the formulation comprises between 0.1 and 7 mg/mL of hypoglycaemic sulfonamide.

The thickener or thickeners of the present formulation make it possible to obtain an adequate viscosity so as to maintain in suspension the micronised particles of active substance and enable an accurate adjustment of the dose by volumetric measurement, for example by means of a dose pipette.

According to one embodiment, the formulation comprises one or more thickeners selected from the group consisting of polysaccharides, cellulose derivatives and carboxyvinyl polymers of the type CARBOPOL. Preferably, the formulation comprises one or more thickeners selected from the group consisting of polysaccharides and cellulose derivatives.

The formulation can comprise one or more thickeners selected from the cellulose derivatives. The cellulose derivatives that can be used as thickeners comprise, but are not limited to, methylcellulose, ethylcellulose, ethylmethylcellulose, carboxymethylcellulose, sodium carboxymethylcellulose and hydroxyalkylcelluloses such as hydroxyethylcellulose, hydroxymethylcellulose, hydroxypropylcellulose and hydroxypropylmethylcellulose, and a combination thereof. Preferably, the formulation comprises hydroxyethylcellulose as a thickener.

The formulation can comprise one or more thickeners selected from the polysaccharides. The polysaccharides that can be used as thickeners comprise, but are not limited to, xanthan gum, tragacanth, carrageenans such as λ-carrageenan, κ-carrageenan or τ-carrageenan, galactomannans such as carob flour, guar flour or tara seed flour, gellan gum, gum arabic, karaya gum, pectins, starch and its derivatives obtained by esterification or etherification, and tamarind, and a combination thereof. Preferably, the formulation comprises xanthan gum as thickener.

The formulation can comprise one or more thickeners selected from polymers of the CARBOPOL type which are polymers of acrylic acid, also called gelling carbomers. These polymers comprise, but are not limited to, CARBOPOL 934P, CARBOPOL 71G, CARBOPOL 971P and CARBOPOL 974P.

The formulation can also comprise, as thickeners, a mixture of one or more cellulose derivatives and one or more polysaccharides. Preferably, the mixture comprises approximately 50% of cellulose derivative(s) and approximately 50% of polysaccharide(s).

In the present document, the term "approximately" refers to a range of values that are ±10% of the specified value. As an example, "approximately 50" comprises values from ±10% of 50, that is to say, values in the range 45 to 55. Preferably, the term "approximately" refers to a range of values that are ±5% of the specified value.

According to a particular embodiment, the formulation comprises hydroxyethylcellulose and xanthan gum as thickeners, preferably approximately 50% of hydroxyethylcellulose and approximately 50% of xanthan gum. Preferably, the formulation does not comprise other thickeners.

The concentration of thickener(s) in the formulation according to the invention can vary according to the nature of said agent or agents and according to the intended method of administration.

When the formulation is intended to be administered by volumetric measure, the concentration is preferably chosen in such a way as to obtain a viscosity comprised between 350 and 450 mPa·s, even more preferably approximately 400 mPa·s.

The formulation according to the invention can comprise between 1 and 50 mg/mL of thickener(s), preferably between 5 and 20 mg/mL, and particularly preferably between 8 and 15 mg/mL. According to a particular embodiment, the formulation comprises approximately 5 mg/mL of hydroxyethylcellulose and approximately 5 mg/mL of xanthan gum.

To prevent the risks of microbial contamination, the formulation according to the invention comprises, preferably, at least one preservative.

The preservatives that can be used in the formulation according to the invention comprise, but are not limited to, benzoic acid and its sodium or potassium salts such as sodium benzoate; parabens such as methylparaben, propylparaben or butylparaben; sorbic acid and its sodium or potassium salts such as potassium sorbate; quaternary ammoniums such as benzalkonium chloride; mercury derivatives such as phenylmercury salts (acetate, borate or nitrate) or thiomersal; and a combination thereof.

For a formulation intended for oral administration, the preservative is preferably selected from the group consisting of benzoic acid and its sodium or potassium salts such as sodium benzoate; parabens such as methylparaben, propylparaben or butylparaben; sorbic acid and its sodium or potassium salts such as potassium sorbate; and a combination thereof.

Preferably, the preservative is suitable for paediatric use. Due to the potential risks to fertility and their metallic taste, parabens are preferably excluded from the present formulation when it is intended for paediatric use, or are used at very low concentrations. Thus, according to one embodiment, the formulation is intended for administration by the oral route and comprises, as a preservative, benzoic acid or one of its sodium or potassium salts, preferably sodium benzoate, or sorbic acid or one of its sodium or potassium salts, preferably potassium sorbate, or a combination thereof. According to a particular embodiment, the formulation comprises benzoic acid or one of its sodium or potassium salts, preferably sodium benzoate, as a preservative. Preferably, the formulation does not comprise another preservative.

For a formulation intended for administration by the ophthalmic route, the preservative is preferably selected from the group consisting of the quaternary ammoniums such as benzalkonium chloride; mercury derivatives such as phenylmercury salts (acetate, borate or nitrate) or thiomersal; and a combination thereof.

The concentration of preservative can be easily adjusted by a person skilled in the art, for example based on the regulatory concentrations indicated in pharmacopoeias. In particular this concentration can vary according to the tightness of the container used, its mode of closure or else the method of storage (in the cold or at room temperature). In particular, the formulation can comprise between 0.5 and 10 mg/mL of preservative(s), preferably approximately 5 mg/mL.

The formulation according to the invention can also comprise a buffer agent to maintain the suspension at a predefined pH comprised between 4 and 8.

For a formulation intended for oral administration, the pH is preferably slightly acidic. In particular, the pH of the formulation can be comprised between 4 and 6, preferably between 4 and 5, and even more preferably between 4.5 and 5.

For a formulation intended for administration by the ophthalmic route, the pH is preferably neutral or slightly basic. In particular, the pH of the formulation can be comprised between 6 and 8, preferably between 7 and 8.

The pH of the formulation according to the invention can also be selected so as to optimise the effects of the preservatives.

The buffer systems that can be used in the formulation according to the invention comprise, but are not limited to, lactic acid/sodium citrate, citric acid/$Na_2HPO_4$, citric acid/sodium citrate, acetic acid/sodium acetate, boric acid, boric acid/sodium acetate, boric acid/sodium propionate and $Na_2HPO_4/NaH_2PO_4$ systems.

In particular, when the formulation is intended for oral administration, the pH is preferably comprised between 4 and 6, and the buffer system can be selected from the group consisting of lactic acid/sodium citrate, citric acid/$Na_2HPO_4$, citric acid/sodium citrate and acetic acid/sodium acetate systems. Preferably, the buffer system is chosen so as to conserve a neutral taste. According to a particular embodiment, the buffer system is composed of sodium citrate and lactic acid. Preferably, the formulation comprises between 5 and 10 mg/mL of sodium citrate, and even more preferably approximately 7.5 mg/mL.

When the formulation is intended for ophthalmic administration, the pH is preferably comprised between 6 and 8, and the buffer system is preferably selected from the group consisting of acetic acid/sodium acetate, boric acid, boric acid/sodium acetate, boric acid/sodium propionate and $Na_2HPO_4/NaH_2PO_4$ systems.

The formulation according to the invention preferably has an osmolality less than 400 mOsm/L. According to one embodiment, the formulation according to the invention has an osmolality less than 350 mOsm/L, preferably less than 300 mOsm/L. According to a particular embodiment, the formulation is particularly suitable for use in premature infants and has an osmolality less than 250 mOsm/L in order to prevent the appearance of digestive disorders.

Although the inventors have observed that the formulation according to the invention has an acceptable taste, it is possible to add flavouring. The formulation according to the invention can therefore additionally comprise a flavour such as strawberry, raspberry, banana, lemon or caramel flavour.

The formulation can also additionally comprise a colouring agent, in particular to make it more acceptable to children. Preferably, the colouring agent is used to strengthen the credibility of the flavour (for example a pink colouring agent for strawberry flavour).

According to a preferred embodiment, the formulation comprises neither flavouring agent nor colouring agent.

The diluent used for the formulation according to the invention is preferably selected so as to have a neutral taste. According to a preferred embodiment, the diluent is water.

According to a particular embodiment, the formulation according to the invention is a liquid pharmaceutical formulation comprising micronised particles of hypoglycaemic sulfonamide, preferably glibenclamide, 90%, or at least 90%, of the particles having a size less than 30 µm, hydroxyethylcellulose and xanthan gum as thickeners, sodium benzoate as a preservative, and a buffer system composed of sodium citrate and lactic acid.

According to a preferred embodiment, the formulation according to the invention is a liquid pharmaceutical formulation comprising between 0.1 and 10 mg/mL, preferably between 0.5 and 7 mg/mL, of micronised particles of hypoglycaemic sulfonamide, preferably glibenclamide, 90%, or at least 90%, of the particles having a size less than 30 µm, approximately 5 mg/mL of hydroxyethylcellulose, approximately 5 mg/mL of xanthan gum, approximately 5 mg/mL of sodium benzoate, and a buffer system composed of sodium citrate and lactic acid maintaining a pH at approximately 4.8. Preferably the formulation comprises approximately 7.5 mg/mL of sodium citrate.

The formulation according to the invention can be packaged in a multi-dose or single-dose container. The formulation according to the invention is preferably packaged in a container comprising, or being associated with, a volumetric delivery system such as a dose pipette, a dosing syringe, a dropper or a system delivering uni-dose drops.

According to a preferred embodiment, the formulation is intended to be administered by the oral route.

According to another embodiment, the formulation is intended to be administered by the ophthalmic route, preferably by topical application in the eye.

Depending on the application considered and the patient to be treated, the formulation according to the invention can also be administered by the rectal or vaginal route.

The present invention also relates to a method for preparing the pharmaceutical formulation according to the invention comprising the steps consisting of:
- mixing the buffer system and the diluent, preferably water;
- adding the micronised particles and mixing until obtaining a homogeneous distribution of the particles;
- adding the thickener(s) and shaking the preparation until obtaining a homogeneous gel;
- allowing the preparation to stand until reaching the desired viscosity;
- adjusting the pH, if necessary; and
- adjusting the final volume by adding the diluent.

Optionally, if the formulation comprises a preservative, it is dissolved in the diluent before adding the buffer system.

The present invention also relates to a formulation according to the invention for use in the treatment of diseases in humans and animals.

In particular, the formulation according to the invention is suitable for use in the treatment of diseases in infants, particularly premature infants, young children and persons, in particular elderly persons, for whom taking tablets may be difficult. Taking tablets can be made difficult in particular by swallowing disorders which are common in the elderly and can lead to suffocation (choking). Thus, the formulation according to the invention is particularly suitable for use in the treatment of diseases in infants, particularly premature infants, young children, persons suffering from swallowing disorders and the elderly.

Preferably, the formulation according to the invention is used to treat infants and/or young children. According to one embodiment, the young children are less than 12 years old, preferably less than 8 years old. According to one embodiment, the infants are less than 2 years old and can be term or premature infants. Preferably, the infants are less than 1 year old, and in an especially preferred manner, less than 8, 6, 4, 2 or 1 month old. According to a particular embodiment, the infants are premature infants born before 32 weeks of gestation, preferably before 28 weeks of gestation.

The formulation according to the invention can also be used in the treatment of diseases in animals, preferably mammals. In particular the animal can be a pet animal or a farm animal, in particular a dog, a cat, a horse, a cow, a sheep, a goat, a rabbit or a rodent.

The disease to be treated can be selected from the group consisting of type 2 diabetes; monogenic diabetes mellitus such as neonatal diabetes, juvenile diabetes involving the same molecular mechanisms as neonatal diabetes (Sagen et al., 2004; Zung et al., 2004; Codner et al., 2005; Babenko et al., 2006; Pearson et al., 2006), mitochondrial diabetes associated with deafness (MIDD, Maternally Inherited Diabetes and Deafness) or MODY diabetes (Maturity Onset Diabetes of the Young); transient neonatal hyperglycaemia; a neuropsychological, muscular or neurological disorder such as epilepsy, delayed development, muscle weakness, dyspraxia, dyslexia, dystonia, dysphasia or else ocular disorders (Zwaveling-Soonawala et al., 2011; Slingerland et al., 2008; WO 2008/015226); and eye diseases, in particular diseases associated with retinal ischaemia and/or retinal excitotoxicity, such as glaucoma, glaucomatous optic neuropathies without hypertonia, age-related macular degeneration, acute or chronic intraocular inflammation (uveitis, uveoretinitis, choroiditis), ischemic or toxic optic neuropathies, endophthalmitis, infectious retinitis, diabetic retinopathy, retinopathy of prematurity, proliferative ischemic retinopathy, retinitis pigmentosa, retinopathies associated with a haemoglobinopathy, photodegeneration, retinal detachment, retinal and choroid vascular pathologies (stenosis, thrombosis and vascular occlusions), retinal and/or choroid haemorrhage, myopia and hereditary or acquired retinal degeneration (WO 2011/036202).

According to one embodiment, the treated disease is selected from the group consisting of type 2 diabetes, neonatal diabetes, juvenile diabetes involving the same molecular mechanisms as neonatal diabetes, mitochondrial diabetes associated with deafness (MIDD) MODY diabetes, transient neonatal hyperglycaemia, and a neuropsychological, muscular or neurological disorder. According to a particular embodiment, the treated disease is selected from the group consisting of type 2 diabetes, neonatal diabetes, juvenile diabetes involving the same molecular mechanisms as neonatal diabetes, transient neonatal hyperglycaemia, and a neuropsychological, muscular or neurological disorder. Preferably, the treated disease is selected from the group consisting of type 2 diabetes, neonatal diabetes and transient neonatal hyperglycaemia. In an especially preferred manner, the treated disease is selected from the group consisting of type 2 diabetes and neonatal diabetes. According to this embodiment, the formulation is preferably administered by the oral route.

According to another embodiment, the treated disease is an ophthalmological disease, preferably a disease associated with retinal ischaemia and/or retinal excitotoxicity. According to this embodiment, the formulation is preferably administered by the ophthalmic route, in particular by topical application, that is to say, on the surface of the eye.

The present invention also relates to a method for treating a disease such as defined above, comprising administering a therapeutically effective dose of the formulation according to the invention to a patient with said disease, the patient preferably being an infant, a young child, a person with a swallowing disorder or an elderly person.

Examples of Aspects of the Invention

1. Liquid pharmaceutical formulation comprising micronised particles of a hypoglycaemic sulfonamide, 90% of the particles having a size less than 30 µm, at least one thickener, and a buffer system maintaining the pH of said formulation between 4 and 8.
2. Formulation according to aspect 1, wherein the formulation comprises at least one thickener selected from the group consisting of polysaccharides and cellulose derivatives.
3. Formulation according to aspect 1 or 2, wherein the formulation comprises hydroxyethylcellulose and xanthan gum as thickeners.
4. Formulation according to any one of the previous aspects, wherein the formulation comprises at least one preservative, preferably sodium benzoate.
5. Formulation according to any one of the previous aspects, wherein the formulation comprises a buffer system maintaining the formulation at a pH comprised between 4.5 and 5.5, preferably a buffer system composed of sodium citrate and lactic acid.
6. Formulation according to any one of the previous aspects, wherein the hypoglycaemic sulfonamide is selected from the group consisting of glibenclamide, chlorpropamide, glibornuride, gliclazide, glimepiride, glipizide, glybutamide, glybuzole, glycyclamide, glymidine sodium, metahexamide, phenbutamide, gliquidone, tolbutamide, tolazamide, acetohexamide, carbutamide, glyclopyramide and glisoxepide, and a combination thereof.

7. Formulation according to any one of the previous aspects, wherein the hypoglycaemic sulfonamide is glibenclamide.
8. Formulation according to any one of the previous aspects, wherein 90% of the micronised particles have a size less than 10 μm.
9. Formulation according to any one of the previous aspects, wherein the formulation has a viscosity comprised between 350 and 450 mPa·s.
10. Formulation according to any one of the previous aspects, wherein the formulation comprises between 0.01 and 100 mg/mL of hypoglycaemic sulfonamide.
11. Formulation according to any one of the previous aspects, wherein the formulation comprises between 0.1 and 10 mg/mL of glibenclamide, approximately 5 mg/mL of hydroxyethylcellulose, approximately 5 mg/mL of xanthan gum, approximately 5 mg/mL of sodium benzoate, and a buffer system composed of sodium citrate and lactic acid maintaining a pH at approximately 4.8.
12. Formulation according to any one of the previous aspects, wherein the formulation is packaged in a container comprising, or being associated with, a volumetric delivery system, or in a single-dose container.
13. Formulation according to any one of the previous aspects, wherein the formulation is intended for administration by the oral route or by the ophthalmic route.
14. Formulation according to any one of the previous aspects for a use in the treatment of diseases in humans, preferably an infant, a young child or a person for whom taking tablets is difficult, or in animals.
15. Formulation according to aspect 14, wherein the disease is selected from the group consisting of type 2 diabetes, neonatal diabetes and juvenile diabetes involving the same molecular mechanisms as those of neonatal diabetes, a neuropsychological, muscular or neurological disease and an ophthalmological disease.

The following examples are given for purposes of illustration and not by way of limitation.

EXAMPLES

The inventors have developed a glibenclamide formulation having the form of an odorless white suspension with a neutral taste and without any bitterness. This formulation allows envisioning its use in infants and young children without having to add flavouring or colouring.

Example 1 of the Formulation According to the Invention

| Components | Unit quantity for 5 mL |
| --- | --- |
| Glibenclamide | 3 mg |
| Hydroxyethylcellulose (Natrosol 250G Pharm) | 25 mg |
| Xanthan gum | 25 mg |
| Sodium benzoate | 25 mg |
| Lactic acid | qs pH 4.8 |
| Sodium citrate | 37.5 mg |
| Purified water | qs 5 mL |

This formulation is particularly suitable for use in infants.

Example 2 of the Formulation According to the Invention

| Components | Unit quantity for 5 mL |
| --- | --- |
| Glibenclamide | 30 mg |
| Hydroxyethylcellulose (Natrosol 250G Pharm) | 25 mg |
| Xanthan gum | 25 mg |
| Sodium benzoate | 25 mg |
| Lactic acid | qs pH 4.8 |
| Sodium citrate | 37.5 mg |
| Purified water | qs 5 mL |

This formulation is particularly suitable for use in young children.

The association of xanthan gum/hydroxyethylcellulose permits a good maintenance in suspension of the active ingredient by both xanthan gum, which has high thixotropic power, and by hydroxyethylcellulose, which maintains a level of viscosity adapted to delivery through a dosing pipette.

Microbiological protection of the suspension is ensured by sodium benzoate. To guarantee the efficiency of this preservative, a pH buffer system is added to the formulation to give the solution a slightly acidic pH of 4.8. The pH buffer is formed of a mixture of lactic acid/sodium citrate. This buffer pair was selected to give the preparation a taste as neutral as possible.

As this is a paediatric medicament intended for the treatment of glycaemic disorders, no sugar-based sweetener or sweetening agent was added. In spite of this the product has a neutral taste without bitterness. No flavouring was considered necessary to make the product acceptable to very young children.

The formulations of examples 1 and 2 were subjected to stability tests and satisfy the criteria of the Pharmacopée Européenne (7$^{th}$ edition) with a stability period of at least 18 months.

In particular, these formulations were found to comply with the requirements of the Pharmacopée Européenne concerning uniformity of mass of the delivered dose of glibenclamide (Ph. Eur. 2.9.27).

Example 3

Three different glibenclamide formulations were administered orally to 18 healthy adult volunteers after an overnight 10-hour fast. Each volunteer received a single dose of 5 mg of glibenclamide and mean plasma concentrations were monitored for 36 hours. To avert any risk of hypoglycaemia, the volunteers were given a 10% glucose infusion, at a dose of 100 mL/hour, 30 minutes before administration of glibenclamide and for 3.5 hours afterwards.

The first formulation was obtained by crushing a DAONIL tablet containing 5 mg of glibenclamide in water.

The second formulation corresponds to the formulation according to example 1 above (3 mg/5 mL of glibenclamide, or 8.33 mL for 5 mg of glibenclamide).

The third formulation corresponds to the formulation according to example 2 above (30 mg/5 mL of glibenclamide, or 0.83 mL for 5 mg of glibenclamide).

The mean plasma concentration profiles of the three formulations are shown in FIG. 1.

These results show first of all that the peak plasma concentrations observed with the formulations according to the invention are almost two times higher than that obtained with the formulation comprising the crushed tablet.

Moreover, the formulations according to the invention lead to a peak plasma concentration 2.5 hours after administration, whereas for the formulation obtained with the crushed tablet, the peak was not reached until 4 hours after administration.

These results therefore demonstrate that the formulations according to the invention display improved pharmacokinetic properties in comparison with the formulation obtained by crushing a DAONIL tablet in water.

REFERENCES

Babenko et al. Activating mutations in the ABCC8 gene in neonatal diabetes mellitus. N Engl J Med, 2006 Aug. 3; 355(5):456-66.

Codner, E., et al., High-dose glibenclamide can replace insulin therapy despite transitory diarrhea in early-onset diabetes caused by a novel R201L Kir6.2 mutation. Diabetes Care, 2005; 28(3):758-9.

Liss B, Roeper J. Molecular physiology of neuronal K-ATP channels. Mol Membr Biol, 2001; 18:117-127.

Pearson et al. Switching from insulin to oral sulfonylureas in patients with diabetes due to Kir6.2 mutations. N Engl J Med, 2006 Aug. 3; 355(5):467-77).

Sagen, J. V., et al. Permanent neonatal diabetes due to mutations in KCNJ11 encoding Kir6.2: patient characteristics and initial response to sulfonylurea therapy. Diabetes, 2004; 53(10):2713-8.

Slingerland et al. Sulphonylurea therapy improves cognition in a patient with the V59M KCNJ11 mutation. Diabet Med, 2008 March; 25(3):277-81.

Zung, A., et al. Glibenclamide treatment in permanent neonatal diabetes mellitus due to an activating mutation in Kir6.2. J Clin Endocrinol Metab, 2004; 89(11):5504-7.

Zwaveling-Soonawala et al. Successful transfer to sulfonylurea therapy in an infant with developmental delay, epilepsy and neonatal diabetes (DEND) syndrome and a novel ABCC8 gene mutation. Diabetologia, 2011; Feb.; 54(2):469-71.

The invention claimed is:

1. A method of treating epilepsy in humans or animals comprising administering a formulation to a human or animal having said disease, wherein said formulation is a liquid pharmaceutical formulation comprising between 0.5 and 7 mg/mL of micronized particles of glibenclamide, between 4.5 and 5.5 mg/mL of hydroxyethylcellulose, between 4.5 and 5.5 mg/mL of xanthan gum, a buffer system maintaining the pH of said formulation between 4.5 and 5.5, and between 4.5 and 5.5 mg/mL of sodium benzoate, wherein said formulation has osmolality below 400 mOsm/L, wherein the buffer system comprises lactic acid and between 6.75 and 8.25 mg/mL sodium citrate, wherein at least 90% of the micronized particles have a size less than 30 μm, and wherein said formulation lacks a sugar-based sweetener.

2. The method according to claim 1, wherein the formulation is administered by the oral route.

3. The method according to claim 1, wherein said formulation comprises between 0.6 and 6 mg/mL of glibenclamide, approximately 5 mg/mL of hydroxyethylcellulose, approximately 5 mg/mL of xanthan gum, approximately 5 mg/mL of sodium benzoate, and a buffer system composed of lactic acid and approximately 7.5 mg/mL sodium citrate and maintaining a pH at approximately 4.8.

4. The method according to claim 1, said formulation lacking a flavouring agent and a colouring agent.

5. The method according to claim 1, wherein the formulation has a pH of approximately 4.8.

6. The method according to claim 1, wherein said formulation is administered to a human selected from the group consisting of an infant, a young child, a person suffering from swallowing disorders and an elderly person.

* * * * *

UNITED STATES PATENT AND TRADEMARK OFFICE
CERTIFICATE OF CORRECTION

| | | |
|---|---|---|
| PATENT NO. | : 11,911,505 B2 | Page 1 of 1 |
| APPLICATION NO. | : 17/412305 | |
| DATED | : February 27, 2024 | |
| INVENTOR(S) | : Marianne Berdugo Polak | |

It is certified that error appears in the above-identified patent and that said Letters Patent is hereby corrected as shown below:

In the Specification

<u>Column 6,</u>
Line 11, "or τ-carrageenan" should read --or ι-carrageenan--

Signed and Sealed this
Seventeenth Day of September, 2024

Katherine Kelly Vidal
*Director of the United States Patent and Trademark Office*